(12) United States Patent
Hellberg et al.

(10) Patent No.: US 6,342,524 B1
(45) Date of Patent: Jan. 29, 2002

(54) USE OF NON-STEROIDAL ANTI-INFLAMMATORY AGENTS IN COMBINATION WITH COMPOUNDS THAT HAVE FP PROSTAGLANDIN AGONIST ACTIVITY TO TREAT GLAUCOMA AND OCULAR HYPERTENSION

(75) Inventors: Mark R. Hellberg, Arlington, TX (US); Jon C. Nixon, Asheboro, NC (US)

(73) Assignee: Alcon Manufacturing, Ltd., Fort Worth, TX (US)

( * ) Notice: Subject to any disclaimer, the term of this patent is extended or adjusted under 35 U.S.C. 154(b) by 0 days.

(21) Appl. No.: 09/575,833

(22) Filed: May 22, 2000

Related U.S. Application Data

(63) Continuation-in-part of application No. 08/994,903, filed on Dec. 19, 1997, now Pat. No. 6,066,671.

(51) Int. Cl.$^7$ .............................................. A61K 31/215

(52) U.S. Cl. ...................... 514/530; 514/567; 514/573; 514/619; 514/913

(58) Field of Search ................................ 514/530, 567, 514/573, 619, 913

(56) References Cited

U.S. PATENT DOCUMENTS

| | | | |
|---|---|---|---|
| 5,093,329 A | 3/1992 | Woodward | |
| 5,151,444 A | 9/1992 | Ueno et al. | |
| 5,422,368 A | 6/1995 | Stjernschantz et al. | |
| 5,474,985 A | 12/1995 | Polansky et al. | |
| 5,475,034 A | 12/1995 | Yanni et al. | |
| 5,510,383 A | 4/1996 | Bishop et al. | |
| 5,565,492 A | 10/1996 | DeSantis et al. | |
| 5,599,535 A | 2/1997 | Polansky et al. | |
| 5,606,043 A | 2/1997 | Nguyen et al. | |
| 5,607,966 A | 3/1997 | Hellberg et al. | |
| 5,627,209 A | 5/1997 | DeSantis et al. | |
| 5,665,773 A | 9/1997 | Klimko et al. | |
| 5,698,733 A | 12/1997 | Hellberg et al. | |
| 5,721,273 A | 2/1998 | Sallee et al. | |
| 5,750,564 A | 5/1998 | Hellberg et al. | |
| 5,807,892 A | 9/1998 | Klimko et al. | |
| 5,814,660 A | 9/1998 | Selliah | |
| 5,866,602 A | 2/1999 | Selliah | |
| 5,925,673 A | 7/1999 | Hellberg et al. | |
| 5,994,397 A | 11/1999 | Selliah et al. | |
| 6,025,392 A | 2/2000 | Selliah et al. | |
| 6,066,671 A | * 5/2000 | Yanni et al. ................. | 514/619 |
| 6,107,343 A | * 8/2000 | Sallman et al. ............. | 514/567 |
| 6,169,111 B1 | * 1/2001 | Zinke et al. | |
| 6,172,109 B1 | * 1/2001 | Zinke et al. | |

FOREIGN PATENT DOCUMENTS

| | | |
|---|---|---|
| EP | 0221753 A2 | 5/1987 |
| GB | 2059963 A | 4/1981 |
| WO | WO 9208465 | 5/1992 |
| WO | WO 9517178 | 6/1995 |
| WO | WO 9614411 | 5/1996 |
| WO | WO 9640102 | 12/1996 |
| WO | WO 9640103 | 12/1996 |
| WO | WO 00/25771 | 5/2000 |

OTHER PUBLICATIONS

Adam, et al., "Recurrent Mutations in a Single Exon Encoding the Evolutionarily Conserved Olfactomedin–Homology Domain of TIGR in Familial Open–Angle Glaucoma," Human Molecular Genetics, 6(12):2091–2097 (1997).

Akarsu, et al., "A Second Locus (GLC3B) for Primary Congenital Glaucoma (Buphthalmos) Maps to the 1p36 Region," Human Molecular Genetics, 5(8):1199–1203 (1996).

Alm, "The Potential of Prostaglandin Derivatives in Glaucoma Therapy,"*Current Opinion in Ophthalmology*, 4(11):44–50 (1993).

Andersen, et al., "A Gene Responsible for the Pigment Dispersion Syndrome Maps to Chromosome 7q35–q36," Arch. Ophthalmol., 115:384–388 (1997).

Clark, et al., "Glucocorticoid–Induced Formation of Cross–Linked Actin Networks in Cultured Human Trabecular Meshwork Cells," Invest. Ophthalmol. Vis. Sci., 35:281–294 (1994).

Clark, "Current trends in antiglaucoma therapy,"*Emerging Drugs*, 4:333–353 (1999).

Giuffre, "The Effects of Prostaglandin F$_{2\alpha}$ the Human Eye," *Graefe's Archive Ophthalmology*, 222:139–141 (1985).

Graff, et al., "Confirmation of Linkage to 1q21–31 in a Danish Autosomal Dominant Juvenile–Onset Glaucoma Family and Evidence of Genetic Heterogeneity," Hum. Genet., 96:285–289 (1995).

Kerstetter et al., "Prostaglandin F$^{2\alpha}$–Isopropylester Lowers Intraocular Pressure Without Decreasing Aqueous Humor Flow," *American Journal of Ophthalmology*, volume 105, pp. 30–34 (1988).

Kubota, et al., "A Novel Myosin–like Protein (Myocilin) Expressed in the Connecting Cilium of the Photoreceptor: Molecular Cloning, Tissue Expression, and Chromosomal Mapping, " Genomics, 41:360–369 (1997).

Meyer, et al., "Age–Dependent Penetrance and Mapping of the Locus for Juvenile and Early–Onset Open–Angle Glaucoma on Chromosome 1q (GLC1A) in a French Family," Hum. Genet., 98:567–571 (1996).

Miyake et al., "Latanoprost accelerates disruption of blood–aqueous barrier and the incidence ofangiographic cystoid macular edema in early postoperative pseudophakis," *Arch. Ophthl*, 117(1):34–40 (1999).

(List continued on next page.)

*Primary Examiner*—Zohreh Fay
(74) *Attorney, Agent, or Firm*—Barry L. Copeland

(57) ABSTRACT

Disclosed are methods and compositions for the treatment of glaucoma and ocular hypertension, comprising the administration of a prostaglandin analog and a prostaglandin synthesis inhibitor.

6 Claims, 2 Drawing Sheets

OTHER PUBLICATIONS

Morissette, et al., "A Common Gene for Juvenile and Adult–Onset Primary Open–Angle Glaucomas Confined on Chromosome 1q," Am. J. Hum. Genet., 56:1431–1442 (1995).

Nakajima, et al., "Effects of prostaglandin $D_2$ and its analogue, BW245C, on intraocular pressure in humans," *Graefe's Archive Ophthalmology* 229:411–413 (1991).

Ortego, et al., "Cloning and Characterization of Substrated cDNAs from a Human Ciliary Body Library Encoding TIGR, a Protein Involved in Juvenile Open Angle Glaucoma with Homology to Myosin and Olfactomedin," FEBS Letters, 413:349–353 (1997).

Polansky, et al., "In Vitro Correlates of Glucocorticoid Effects on Intracular Pressure," Glaucoma Update IV (1991).

Polansky, et al., "Cellular Pharmacology and Molecular Biology of the Trabecular Meshwork Inducible Glucocorticoid Response Gene Product," Ophthalmologica, 211:126–139 (1997).

Richards, et al., "Mapping of a Gene for Autosomal Dominant Juvenile–Onset Open–Angle Glaucoma to Chromosome 1q," Am. J. Hum. Genet., 54:62–70 (1994).

Rozsival, et al., "Aqeous Humour and Plasma Cortisol Levels in Glaucoma and Cataract Patients," Current Eye Research, 1:391–396 (1981).

Sarfarazi, et al., "Assignment of a Locus (GLC3A) for Primary Congenital Glaucoma (Buphthalmos) to 2p21 and Evidence for Genetic Heterogeneity," Genomics, 30:171–177 (1995).

Schwartz, et al., "Increased Plasma Free Cortisol in Ocular Hypertension and Open Angle Glaucoma," Arch. Ophthalmol., 105:1060–1065 (1987).

Sheffield, et al., "Genetic Linkage of Familial Open Angle Glaucoma to Chromosome 1q21–q31," Nature Genetics, 4:47–50 (1993).

Sommer A, et al. Relationship between intraocular pressure and primary open angle glaucoma among white and black Americans. Arch. Ophthalmol. 109:1090–1095, (1991).

Stoilova, et al., "Localization of a Locus (GLC1B) for Adult–Onset Primary Open Angle Glaucoma to the 2cen–q13 Region," Genomics 36:142–150 (1996)..

Stone, et al., "Identification of a Gene That Causes Primary Open Angle Glaucoma," Science, 275:668–670 (1997).

Sunden, et al., "Fine Mapping of the Autosomal Dominant Juvenile Open Angle Glaucoma (GLC1A) Region and Evaluation of Candidate Genes," Genome Research, 6: 862–869 (1996).

Wiggs, et al., "Genetic Linkage of Autosomal Dominant Juvenile Glaucoma to 1q21–q31 in Three Affected Pedigrees," Genomics, 21:299–303 (1994).

Wilson, et al., Dexamethasone Induced Ultrastructural Changes in Cultured Human Trabecular Meshwork Cells, Cur. Eye Res. 12:783–793 (1993).

Wirtz, et al., "Mapping a Gene for Adult–Onset Primary Open–Angle Glaucoma to Chromosome 3q," Am. J. Hum. Genet., 60:296–304 (1997).

* cited by examiner

Maximum Potential Drug Concentration
in Various Ocular Compartments

| Compartment | Concentration ($\mu M$) |
| --- | --- |
| Cornea | 200 |
| Iris-Ciliary Body | 29 |
| Aqueous Humor | 24 |
| Choroid | 0.4 |
| Retina | 0.2 |

FIG. 2

USE OF NON-STEROIDAL ANTI-INFLAMMATORY AGENTS IN COMBINATION WITH COMPOUNDS THAT HAVE FP PROSTAGLANDIN AGONIST ACTIVITY TO TREAT GLAUCOMA AND OCULAR HYPERTENSION

CROSS REFERENCE TO RELATED APPLICATION

This application is a continuation-in-part of U.S. application Ser. No. 08/994,903 filed Dec. 19, 1997, now U.S. Pat. No. 6,066,671.

FIELD OF THE INVENTION

This invention is directed to the use of non-steroidal anti-inflammatory agents, and especially certain non-steroidal cyclooxygenase inhibitors in combination with FP prostaglandin agonists for treating glaucoma and/or ocular hypertension in an individual.

BACKGROUND OF THE INVENTION

The glaucomas are a heterogeneous group of optic neuropathies characterized by cupping of the optic nerve head, thinning of the retinal nerve fiber layer due to loss of retinal ganglion cells, and specific pathognomonic changes in visual fields. Elevated intraocular pressure (IOP) is a very important risk factor for the development of most common forms of glaucoma (Sommer A, et al., "Relationship Between Intraocular Pressure and Primary Open Angle Glaucoma Among White and Black Americans," *Arch. Ophthalmol.*, 109:1090–1095 (1991)).

A family history of glaucoma also is an important risk factor for the development of glaucoma. It appears that a significant portion of glaucoma is inherited (or at least the risk for developing glaucoma is inherited) although it is often difficult to establish clear inheritance patterns for most of the glaucomas because of the disease onset late in life and the slowly progressive clinical manifestations of the disease. Despite these problems, a number of families with heritable forms of glaucoma have been identified and these families have been used to map a variety of glaucoma genes (Sheffield, et al., "Genetic Linkage of Familial Open Angle Glaucoma to Chromosome 1q21–q31," *Nature Genetics*, 4:47–50 (1993); Sarfarazi, et al., "Assignment of a Locus (GLC3A) for Primary Congenital Glaucoma (Buphthalmos) to 2p21 and Evidence for Genetic Heterogeneity," *Genomics*, 30:171–177 (1995); Akarsu, et al., "A Second Locus (GLC3B) for Primary Congenital Glaucoma (Buphthalmos) Maps to the 1p36 Region," *Human Molecular Genetics*, 5(8):1199–1203 (1996); Stoilova, et al., "Localization of a Locus (GLC1B) for Adult-Onset Primary Open Angle Glaucoma to the 2cen-q13 Region," *Genomics*, 36:142–150 (1996); Wirtz, et al., "Mapping a Gene for Adult-Onset Primary Open-Angle Glaucoma to Chromosome 3q," *Am. J. Hum. Genet.*, 60:296–304 (1997); Andersen, et al., "A Gene Responsible for the Pigment Dispersion Syndrome Maps to Chromosome 7q35–q36," *Arch. Ophthalmol.*, 115:384–388 (1997). The first glaucoma gene mapped (GLC1A) was in a large family with autosomal dominant inherited juvenile glaucoma (JG). This disease is characterized by an early disease onset (at the age of late teens to early 20s), relatively high IOPs, and general resistance to conventional pharmacological IOP lowering therapy. The GLC1A gene was mapped by positional cloning and linkage analysis to chromosome 1q22–q25 (Sheffield et al, Id., and a number of other groups have confirmed the 1q location of this juvenile glaucoma gene (Richards, et al., "Mapping of a Gene for Autosomal Dominant Juvenile-Onset Open-Angle Glaucoma to Chromosome 1q," *Am. J. Hum. Genet.*, 54:62–70 (1994); Morissette, et al., "A Common Gene for Juvenile and Adult-Onset Primary Open-Angle Glaucomas Confined on Chromosome 1q," *Am. J. Hum. Genet.*, 56:1431–1442 (1995); Wiggs, et al., "Genetic Linkage of Autosomal Dominant Juvenile Glaucoma to 1q21–q31 in Three Affected Pedigrees," *Genomics*, 21:299–303 (1994); Meyer, et al., "Age-Dependent Penetrance and Mapping of the Locus for Juvenile and Early-Onset Open-Angle Glaucoma on Chromosome 1q (GLC1A) in a French Family," *Hum. Genet.*, 98:567–571 (1996); Graff, et al., "Confirmation of Linkage to 1q21–31 in a Danish Autosomal Dominant Juvenile-Onset Glaucoma Family and Evidence of Genetic Heterogeneity," *Hum. Genet.*, 96:285–289 (1995). Glaucoma due to the GLC1A gene is hereinafter referred to as GLC1A glaucoma or 1q glaucoma.

The GLC1A gene was identified as encoding a 57 kD protein expressed in the trabecular meshwork (TM) (Stone, et al., "Identification of a Gene That Causes Primary Open Angle Glaucoma," *Science*, 275:668–670 (1997). The expression of the GLC1A gene, and the encoded TM protein, is up-regulated by glucocorticoids (Polansky, et al., "In Vitro Correlates of Glucocorticoid Effects on Intraocular Pressure," *Glaucoma Update IV* (1991); and Polansky, et al., "Cellular Pharmacology and Molecular Biology of the Trabecular Meshwork Inducible Glucocorticoid Response Gene Product," *Ophthalmologica*, 211:126–139 (1997). This TM protein is also known as TIGR (trabecular meshwork inducible glucocorticoid response) (Polansky, Id.). The glucocorticoid-induction of this TM protein has been suggested to be involved in the generation of glucocorticoid-induced ocular hypertension and glaucoma (Polansky, Id.).

The GLC1A gene is expressed in other ocular tissues such as the ciliary epithelium (Ortego, et al., "Cloning and Characterization of Subtracted cDNAs from a Human Ciliary Body Library Encoding TIGR, a Protein Involved in Juvenile Open Angle Glaucoma with Homology to Myosin and Olfactomedin," *FEBS Letters*, 413:349–353 (1997) and the retina (Kubota, et al., "A Novel Myosin-like Protein (Myocilin) Expressed in the Connecting Cilium of the Photoreceptor: Molecular Cloning, Tissue Expression, and Chromosomal Mapping," *Genomics*, 41:360–369 (1997). The gene is referred to by several names including GLC1A (Sheffield, supra; Sunden, et al., "Fine Mapping of the Autosomal Dominant Juvenile Open Angle Glaucoma (GLC1A) Region and Evaluation of Candidate Genes," *Genome Research*, 6:862–869 (1996); Stone, et al., supra, TIGR (Polansky supra; Ortego, supra, and myocilin (Kubota, supra). Mutations in GLC1A are not only responsible for juvenile glaucoma, but also a significant subset of adult onset primary open angle glaucoma (Stone, et al., supra); Adam, et al., "Recurrent Mutations in a Single Exon Encoding the Evolutionarily Conserved Olfactomedin-Homology Domain of TIGR in Familial Open-Angle Glaucoma," *Human Molecular Genetics*, 6(12):2091–2097 (1997). The 1q glaucoma gene (GLC1A) is the subject of Nguyen, et al., U.S. Pat. No. 5,606,043, issued Feb. 25, 1997.

Ocular inflammation is a condition which generally affects the patient with scratchiness, itchiness and/or red eye. Ocular inflammation can be initiated by various insults. For example, ocular inflammation can result from allergic response to various allergens, trauma to the eye, dry eye and surgical complications. Various anti-inflammatory therapies are currently known for the treatment of inflammation, including the topical administration of non-steroidal anti-inflammatory agents such as diclofenac for ophthalmic inflammation. A number of these therapies, from aspirin to the recently commercialized COX II inhibitors, celocoxib and refocoxib, are believed to involve, at least in part, inhibition of prostaglandin synthesis. In addition to the treatment of inflammation, several patent applications have disclosed the use of non-steroidal cyclooxygenase inhibitors to treat intraocular pressure (WO 95/17178) through the action of the compounds on trabecular meshwork cells (WO 96/40103 and WO 96/40102). At least some of the beneficial effects of the non-steroidal cyclooxygenase inhibitors are attributed to the inhibition of the expression of myocilin (or TIGR) which is the gene product of GLC1A.

It is known that trabecular meshwork cells have glucocorticoid receptors and that glucocorticoid binding with these receptors causes a change in trabecular meshwork cell gene expression. Known manifestations of this change include a reorganization of the cytoskeleton (Wilson, et al., "Dexamethasone Induced Ultrastructural Changes in Cultured Human Trabecular Meshwork Cells, *Cur. Eye Res.*, 12:783–793 (1993), and Clark, et al., "Glucocorticoid-Induced Formation of Cross-Linked Actin Networks in Cultured Human Trabecular Meshwork Cells," *Invest. Ophthalmol. Vis. Sci.*, 35:281–294 (1994)) and increased deposition of the extracellular matrix material in trabecular meshwork cells. As a result, the trabecular meshwork becomes "clogged" and unable to perform one of its most critical functions, that is, serving as a gateway for aqueous humor flow from the anterior chamber of the eye. When the aqueous humor flow out of the eye via the trabecular meshwork is diminished, the intraocular pressure of the eye rises. If this state of elevated intraocular pressure (IOP) is maintained or frequently occurs, the optic nerve head can be damaged resulting in the loss of visual field. Loss of visual field is the hallmark symptom associated with glaucoma.

Prostaglandins, which are metabolite derivatives of arachidonic acid, have recently been pursued for possible efficacy in treating glaucoma and lowering IOP. The arachidonic acid cascade is initiated by the conversion of arachidonic acid to prostaglandin $G_2$ and subsequent conversion to prostaglandin $H_2$. Other naturally occurring prostaglandins are derivatives of prostaglandin $H_2$. A number of different types of prostaglandins have been discovered including A, B, D, E, F and I-Series prostaglandins. Of interest in the present invention are combinations of compounds which exhibit similar IOP lowering mechanisms as $PGF_{2\alpha}$, formula (I):

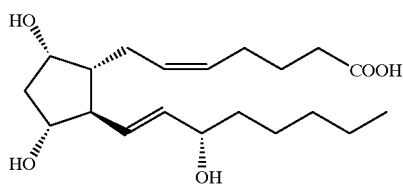

(I)

The relationship of $PGF_{2\alpha}$ receptor activation and IOP lowering effects is not well understood. It is believed that $PGF_{2\alpha}$ receptor activation leads to increased outflow of aqueous humor. Regardless of mechanism, $PGF_{2\alpha}$ and analogs have been shown to lower IOP (Giuffre, The Effects of Prostaglandin $F_{2\alpha}$ the Human Eye, *Graefe's Archive Ophthalmology*, volume 222, pages 139–141 (1985); and Kerstetter et al., Prostaglandin $F_{2\alpha}$-1-Isopropylester Lowers Intraocular Pressure Without Decreasing Aqueous Humor Flow, *American Journal of Ophthalmology*, volume 105, pages 30–34 (1988)). Thus, it has been of interest in the field to develop synthetic $PGF_{2\alpha}$ analogs with IOP lowering efficacy.

Synthetic $PGF_{2\alpha}$-type analogs have been pursued in the art (*Graefe's Archive Ophthalmology*, volume 229, pages 411–413 (1991)). Though $PGF_{2\alpha}$-type molecules lower IOP, these types of molecules have also been associated with undesirable side effects resulting from topical ophthalmic dosing. Such effects include an initial increase in IOP, breakdown of the blood aqueous barrier and conjunctival hyperemia (Alm, The Potential of prostaglandin Derivatives in Glaucoma Therapy, *Current Opinion in Ophthalmology*, volume 4, No. 11, pages 44–50 (1993)). The binding of PGF analogs with the $PGF_{2\alpha}$ receptor may lead to IOP lowering effects, but with fewer or diminished side effects compared to those elicited by the above mentioned $PGF_{2\alpha}$-type analogs.

Attempts have been made by Stjernschantz et al. (U.S. Pat. No. 5,422,368), Woodward et al., (U.S. Pat. No. 5,093, 329), Chan et al. (WO 92/08465) and Ueno et al. (U.S. Pat. No. 5,151,444) to reduce selectively or to eliminate altogether the side effects while maintaining the IOP-lowering effect. The contents of the foregoing U.S. patents are by this reference incorporated herein. Commonly assigned U.S. Pat. Nos. 5,510,383; 5,627,209; 5,665,773; 5,721,273; 5,698, 733; 5,807,892; 5,814,660; 5,866,602; 5,994,397; 6,025, 392; 6,169,111; and 6,172,109 are also by this reference incorporated herein.

Even such modified prostaglandins, however, still often exhibit undesirable side effects. Latanoprost, for example (commercially available from Pharmacia, Inc.) is generally not excessively hyperemic, but it is known to cause iridial hyperpigmentation, as well as darkening of the eyelids and lashes in some patients (secondary side effects). Clark, "Current trends in antiglaucoma therapy," *Emerging Drugs*, 4:333–353 (1999). There remains a need, therefore, for a relatively side effect free prostaglandin therapy.

Use of the non-steroidal anti-inflammatory agents diclofenac sodium and fluorometholone in concurrent administration with the prostaglandin analog, latanoprost has been suggested to reduce the amount of flare and cystoid macular edema associated with the use of the prostaglandin analog in glaucoma therapy. Miyake et al., "Latanoprost accelerates disruption of blood-aqueous barrier and the incidence of angiographic cystoid macular edema in early postoperative pseudophakis," *Arch. Ophthl*, 117(1):34–40 (1999). Commonly assigned U.S. Pat. Nos. 5,607,966; 5,750,564; and 5,607,966, which are by this reference incorporated herein, disclose non-steroidal anti-inflammatory agents useful in the treatment of ocular inflammation.

SUMMARY OF THE INVENTION

Certain non-steroidal cyclooxygenase inhibitors and their pharmaceutical formulations are useful for treating GLC1A glaucoma. The invention is also directed to methods for controlling GLC 1A glaucoma using the non-steroidal cyclooxygenase inhibitors. A further aspect of the invention lies in the discovery that these non-steroidal anti-inflammatory agents and other prostaglandin synthesis inhibitors may be used in combination with prostaglandin analogs to treat glaucoma with reduced side effects.

BRIEF DESCRIPTION OF DRAWINGS

FIG. 2 shows the nepafenac concentration calculated from the data in FIG. 1.

DESCRIPTION OF PREFERRED EMBODIMENTS

Figure 1:
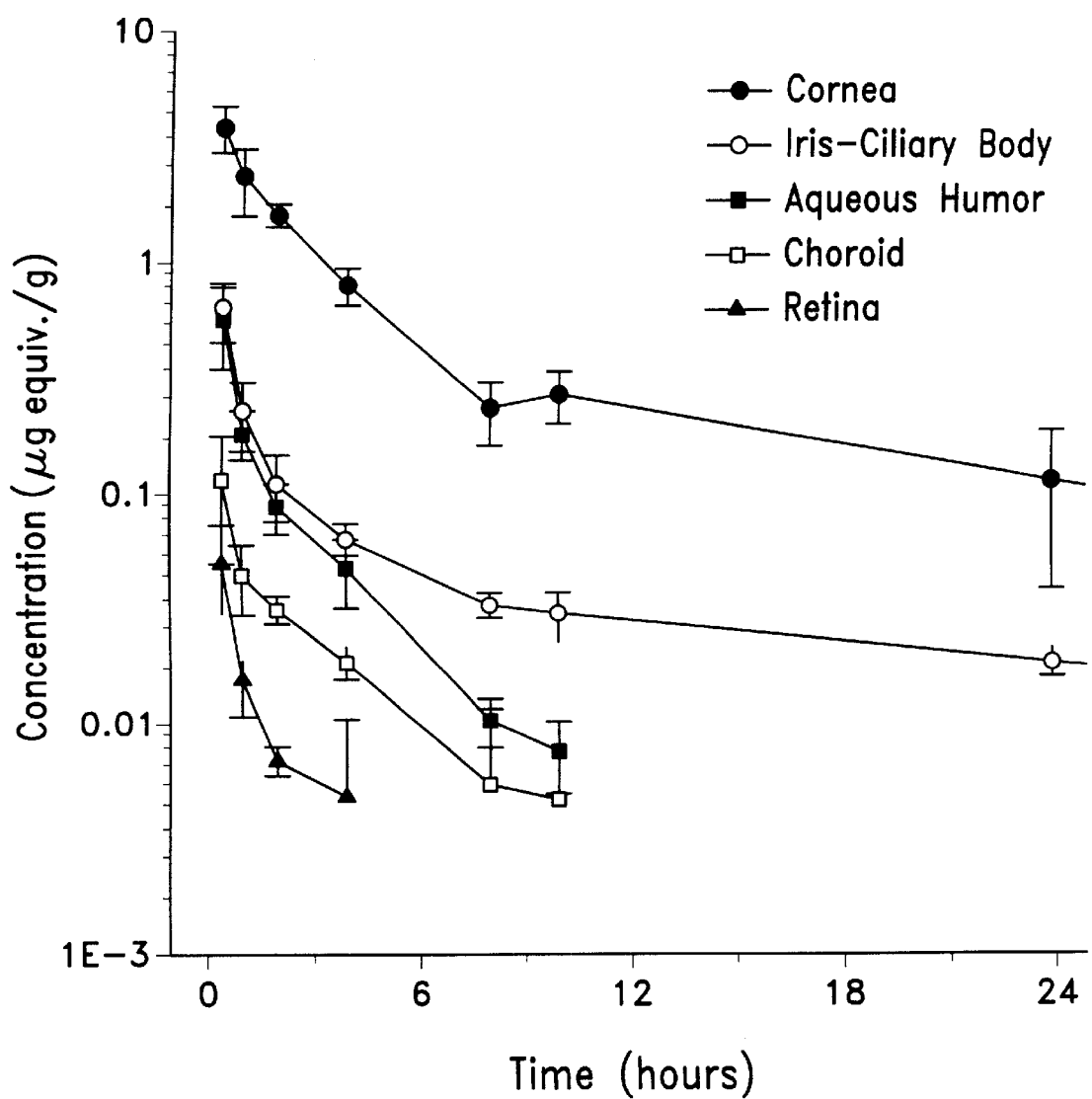
FIG. 1 shows nepafenac concentrations in ocular tissues of rabbits following a single topical dose.

Agents which alter the expression of GLC1A in the glaucomatous eye are expected to lower IOP and thereby prevent or inhibit the glaucomatous optic neuropathy which is being driven by elevated IOP. Glucocorticoids upregulate GLC1A expression in the TM of certain individuals. There have been several reports of elevated levels of the natural glucocorticoid cortisol in the aqueous humor and plasma of glaucoma patients (Schwartz, et al., supra; Rozsival, et al., supra. In addition, certain mutations in GLC1A may alter the expression of GLC1A in the TM tissue of 1q glaucoma patients. Unexpectedly, it has been discovered that certain non-steroidal cyclooxygenase inhibitors inhibit the expression of GLC1A in cultured human TM cells and lower elevated IOP in certain animal models of ocular hypertension. The non-steroidal cyclooxygenase inhibitors act to prevent the expression of GLC1A and the subsequent development of ocular hypertension. While bound by no theories, it is postulated that the secondary side effects of prostaglandin therapy and especially PGF-type prostaglandin therapy, may be attributable to prostaglandin induced prostaglandin synthesis in the eye. The IOP lowering effect of the prostaglandin analogs, however, is believed to result from a direct effect on the target tissue. Thus, in addition to reducing inflammation (flare and cystoid macular edema), prostaglandin synthesis inhibitors, such as the non-steroidal anti-inflammatory agents described herein (whether directly or through an incorporated reference), will ameliorate the undesirable secondary side effects associated with prostaglandin therapy for the treatment of glaucoma, without significantly interfering with the desired IOP lowering.

The present invention is directed, therefore, to methods of treating glaucoma, comprising concurrent or combined administration of therapeutically effective amounts of a prostaglandin analog and a prostaglandin synthesis inhibitor. The preferred methods of the present invention comprise one or more prostagaindin analogs in combination with one or more prostaglandin synthesis inhibitors. Preferred among the prostaglandin analogs are the F-type prostaglandin analogs. Preferred among the prostaglandin synthesis inhibitors are the non-steroidal anti-inflammatory agents, especially those which inhibit PGE synthesis. It will be appreciated, however, that any IOP lowering effective prostaglandin in combination with any prostaglandin synthesis inhibitor for the treatment of glaucoma is within the scope of the present invention.

Many non-steroidal cyclooxygenase inhibitors do not readily penetrate the cornea upon topical administration and, therefore, do not reach therapeutic concentrations in the target tissue, whether that be the trabecular meshwork, iridial melanocytes, or some other tissue.

A series of compounds disclosed in commonly assigned U.S. Pat. No. 5,475,034, which showed no significant non-steroidal anti-inflammatory activity in vitro, exhibit superior corneal penetration leading to improved ocular bioavailability. The estimated concentration within the anterior chamber following topical ocular administration of 0.3% nepafenac to rabbits is 24 $\mu$M (see FIGS. 1 and 2). This concentration, achieved using a simple formulation without penetration enhancers, is in excess of the parent compounds' COX I and COX II $IC_{50}$s. This enhanced bioavailability provides a significant advantage and is unexpected over other non-steroidal anti-inflammatory drugs as well as amide derivatives of non-steroidal anti-inflammatory drugs. The compounds disclosed in the '034 patent, the contents of which are incorporated herein by reference, are ester and amide derivatives of 3-benzoylphenylacetic acid.

The compounds set forth in the '034 patent have the following structure:

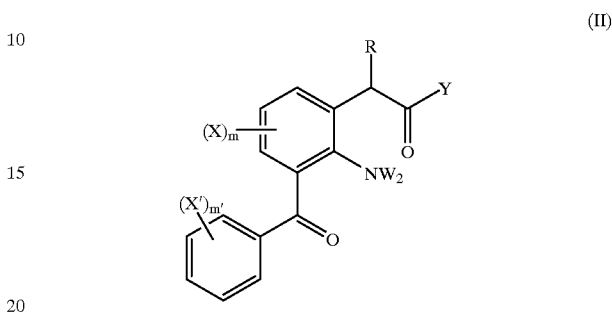

(II)

R=H, $C_{1-4}$ (un)branched alkyl, $CF_3$, $SR^4$

Y=OR', NR"R'

R'=H (except when Y=OR'), $C_{1-10}$ (un)branched alkyl, (un)substituted (substitution as defined by X below), (un)substituted heterocycle (substitution as defined by X below), —$(CH_2)_nZ(CH_2)_{n'}$A n=2–6 n'=1–6

Z=nothing, O, C=O, OC(=O), C(=O)O, C(=O)$NR^3$, $NR^3$C(=O), S(O)$_{n^2}$, $CHOR^3$, $NR^3$ $n^2$=0–2

$R^3$=H, $C_{1-6}$ (un)branched alkyl, (un)substituted aryl (substitution as defined by X below), (un)substituted heterocycle (substitution as defined by X below)

A=H, OH, optionally (un)substituted aryl (substitution as defined by X below), (un)substituted heterocycle (substitution as defined by X below), —$(CH_2)_nOR^3$

R"=H, OH, OR'

X and X' independently=H, F, Cl, Br, I, OR', CN, OH, S(O)$_n$$2R^4$, $CF_3$, $R^4$, $NO_2$ $R^4$=$C_{1-6}$ (un)branched alkyl m=0–3 m'=0–5

W=O, H

Preferred compounds for use as a prostaglandin synthesis inhibitor in the pharmaceutical compositions or methods of the present invention are those of Formula II wherein:

R=H, $C_{1-2}$ alkyl

Y=NR'R"

R'=H, $C_{1-6}$ (un)branched alkyl, —$(CH_2)_nZ(CH_2)_{n'}$A

Z=nothing, O, $CHOR^3$, $NR^3$ $R_3$=H

A=H, OH, (un)substituted aryl (substitution as defined by X below)

X and X' independently=H, F, Cl, Br, CN, $CF_3$, OR', $SR^4$, $R^4$

R"=H $R^4$=$C_{1-4}$ (un)branched alkyl m=0–2 m'=0–2

W=H n=2–4 n'=0–3

The most preferred compounds for use as a prostaglandin synthesis inhibitor in the compositions or methods of the present invention are 2-Amino-3-(4-fluorobenzoyl)-phenylacetamide; 2-Amino-3-benzoyl-phenylacetamide (nepafenac); and 2-Amino-3-(4-chlorobenzoyl)-phenylacetamide.

For the preferred compound, nepafenac, W=H, R=H, Y=NH$_2$, X'=H, X=H, m=3, and m'=5.

The FP-agonists of the present invention are of the following formula (III):

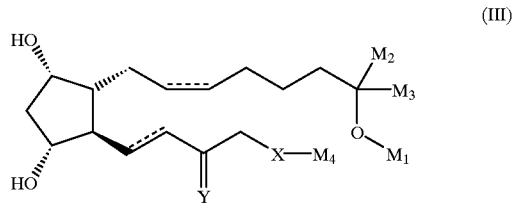

(III)

wherein:

X is CH$_2$ or O;

Y is H and OH or O;

M$_1$ is H, C$_{1-2}$ straight-chain or branched alkyl; C$_{1-12}$ straight chain or branched acyl; C$_{3-8}$ cycloalkyl; a cationic salt moiety; or an acceptable amine moiety;

M$_2$ and M$_3$ are H or taken together are (=O); and

M$_4$ is C$_{3-5}$ alkyl or

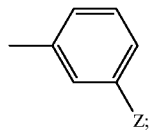

and

Z is H, Cl or CF$_3$;

provided that when M$_2$ and M$_3$ taken together are (=O), then M, cannot be C$_{1-12}$ straight chain or branched acyl; and when M$_2$ and M$_3$ are H, then M$_1$ cannot be a salt or an amine.

The following are preferred FP-agonists of formula (III): latanoprost, travoprost, and UFO-21, as well as, cloprostenol, fluprostenol, 13,14 dihydro-cloprostenol and 13, 14-dihydrofluprostenol and their isopropyl esters and salts. Also preferred is isopropyl [2R(1E,3R),3S(4Z),4R]-7-[Tetrahydro-2-[4-(3-chlorophenoxy)-3-hydroxy-1-butenyl]-4-hydroxy-3-furanyl]-4-heptenoate. The most preferred FP-agonists of the present invention are latanoprost and travoprost.

The FP-agonists of the present invention are known and are either commercially available or may be prepared by known methods to those skilled in the art. Some of the FP-agonists of the present invention are disclosed in European Patent Publication No. 0 639 563 A2, which is incorporated herein by reference to the extent that it discloses methods of synthesizing or obtaining FP-agonists of the present invention.

The prostaglandin analogs and prostaglandin synthesis inhibitors of the present invention may be formulated in various pharmaceutical compositions for administering to humans and other mammals as a treatment of glaucoma or ocular hypertension. As used herein, the term "pharmaceutically effective amount" refers to that amount of a prostaglandin analog which lowers IOP when administered to a patient, or that amount of a prostaglandin synthesis inhibitor which reduces secondary side effects of prostaglandin therapy when administered in conjunction with such therapy. The preferred route of administration is topical. The compounds of the present invention can be administered as solutions, suspensions, or emulsions (dispersions) in an ophthalmically acceptable vehicle. As used herein, the term "ophthalmically acceptable vehicle" refers to any substance or combination of substances which are non-reactive with the compounds and suitable for administration to a patient. Solubilizers and stabilizers are deemed to be non-reactive. Preferred are aqueous vehicles suitable for topical application to the patient's eyes.

In forming compositions for topical administration, the prostaglandin analogs of the present invention are generally formulated as between about 0.00003 to about 0.5 percent by weight (wt %) solutions and the prostaglandin synthesis inhibitors are generally formulated as between about 0.001 to about 1.0 percent by weight (wt %), both in water at a pH between about 4.5 to about 8.0, preferably between about 5.0 and about 7.5. The prostaglandin compounds are preferably formulated as between about 0.0005 to about 0.03 wt % and, most preferably, between about 0.001 and about 0.01 wt %. While the precise regimen is left to the discretion of the clinician, it is recommended that the resulting solution(s) be topically applied by placing one drop in each eye one or two times a day.

Other ingredients which may be desirable to use in the ophthalmic preparations of the present invention include preservatives, co-solvents, and viscosity building agents.

Antimicrobial Preservatives

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Such preservatives are typically employed at a level between about 0.001% and about 1.0% by weight.

Co-Solvents

Prostaglandins, and particularly ester derivatives, typically have limited solubility in water and therefore may require a surfactant or other appropriate co-solvent in the composition. Such co-solvents include: Polysorbate 20, 60 and 80; Pluronic F-68, F-84 and P-103; CREMOPHORE® EL (polyoxyl 35 castor oil); cyclodextrin; or other agents known to those skilled in the art. Such co-solvents are typically employed at a level between about 0.01% and about 2% by weight.

Viscosity Agents

Viscosity greater than that of simple aqueous solutions may be desirable to increase ocular absorption of the active compound, to decrease variability in dispensing the formulations, to decrease physical separation of components of a suspension or emulsion of formulation and/or otherwise to improve the ophthalmic formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and other agents known to those skilled in the art. Such agents are typically employed at a level between about 0.01% and about 2% by weight.

The following examples are illustrative of formulations which can be used according to the present invention, but are not limiting. "Active Agent" means one or more non-steroidal anti-inflammatory agents; described by the structure and definition set forth above.

EXAMPLE 1

| Ingredient | Amount (wt/vol %) |
|---|---|
| Nepafenac | 0.1 |
| Travoprost | 0.004 |
| NCO - 40 | 0.1 |
| Tromethamine | 0.12 |
| Boric acid | 0.3 |
| Mannitol | 4.6 |
| Disodium EDTA (edetate disodium) | 0.1 |
| Benzalkonium Chloride Solution | 0.01 |
| HCl and/or NaOH | pH 7.3–7.4 |
| Purified Water | q.s. to 100% |

EXAMPLE 2

| Component | Concentraton (% w/w/) |
|---|---|
| Nepafenac | 0.1 |
| Latanoprost | 0.005 |
| Carbopol 974P | 0.5 |
| Sodium Chloride | 0.4 |
| Mannitol | 2.4 |
| Tyloxapol | 0.1 |
| EDTA | 0.01 |
| Benzalkonium Chloride | 0.01 |
| NaOH or HCl | QS pH 7.5 |
| Water for injection | QS 100% |

EXAMPLE 3

| Active Agent | 0.01–0.5% |
|---|---|
| Travoprost | 0.0015% |
| Hydroxypropyl Methylcellulose | 0.5% |
| Polysorbate 80 | 0.01% |
| Benzalkonium Chloride | 0.01% + 5% excess |
| Disodium EDTA | 0.01% |
| Dibasic Sodium Phosphate | 0.2% |
| Sodium Chloride | q.s. 290–300 Osm/Kg |
| pH adjustment with NaOH and/or HCl | pH 4.2–7.4 |
| Water | q.s. 100% |

EXAMPLE 4

| Active agent | 0.01–0.5% |
|---|---|
| Latanoprost | 0.005% |

-continued

| Polysorbate 80 | 0.01% |
|---|---|
| Benzalkonium Chloride | 0.01% + 10% excess |
| Disodium EDTA | 0.1% |
| Monobasic Sodium Phosphate | 0.03% |
| Dibasic Sodium Phosphate | 0.1% |
| Sodium Chloride | q.s. 290–300 Osm/Kg |
| pH adjustment with NaOH and/or HCl | pH 4.2–7.4 |
| Water | q.s. 100% |

The invention has been described by reference to certain preferred embodiments; however, it should be understood that it may be embodied in other specific forms or variations thereof without departing from its spirit or essential characteristics. The embodiments described above are therefore considered to be illustrative in all respects and not restrictive, the scope of the invention being indicated by the appended claims rather than by the foregoing description.

We claim:

1. A method of treating glaucoma, comprising administering to an affected eye, an intraocular pressure lowering effective amount of a prostaglandin analog, and a prostaglandin synthesis inhibiting effective amount of a prostaglandin synthesis inhibitor other than diclofenac or fluorometholome.

2. The method of claim 1, wherein the prostaglandin analog is a prostaglandin F agonist and the prostaglandin synthesis inhibitor is a non-steroidal anti-inflammatory agent.

3. The method of claim 2, wherein the non-steroidal anti-inflammatory agent is a compound of the following formula:

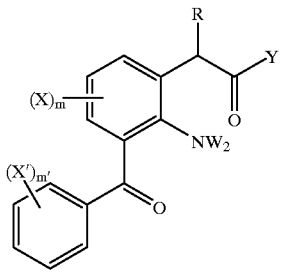

R=H, $C_{1-4}$ (un)branched alkyl, $CF_3$, $SR^4$

Y=OR', NR"R'

R'=H (except when Y=OR'), $C_{1-10}$ (un)branched alkyl, (un)substituted (substitution as defined by X below), (un)substituted heterocycle (substitution as defined by X below), —$(CH_2)_n Z(CH_2)_{n'} A$ n=2–6 n'=1–6

Z=nothing, O, C=O, OC(=O), C(=O)O, C(=O)$NR^3$, $NR^3 C(=O)$, $S(O)_{n^2}$, $CHOR^3$, $NR^3$ $n^2$=0–2

$R^3$=H, $C_{1-6}$ (un)branched alkyl, (un)substituted aryl (substitution as defined by X below), (un)substituted heterocycle (substitution as defined by X below)

A=H, OH, optionally (un)substituted aryl (substitution as defined by X below), (un)substituted heterocycle (substitution as defined by X below), —$(CH_2)_n OR^3$

R"=H, OH, OR'

X and X' independently=H, F, Cl, Br, I, OR', CN, OH, $S(O)_{n^2} R^4$, $CF_3$, $R^4$, $NO_2$ $R^4 = C_{1-6}$ (un)branched alkyl m=0–3 m'=0–5

W=O, H.

4. The method of claim 3, wherein the prostaglandin analog and the prostaglandin synthesis inhibitor are administered as a combination product.

5. The method of claim 4, wherein the prostaglandin F agonist is selected from the group consisting of latanoprost, travoprost, unoprostone, and [2R(1E,3R),3S(4Z),4R]-7-[Tetrahydro-2-[4-(3-chlorophenoxy)-3-hydroxy-1-butenyl]-4-hydroxy-3-furanyl]-4-heptenoate, and wherein the prostaglandin synthesis inhibitor is selected from the group consisting of: 2-Amino-3-(4-fluorobenzoyl)-phenylacetamide; 2-Amino-3-benzoyl-phenylacetamide (nepafenac); and 2-Amino-3-(4-chlorobenzoyl)-phenylacetamide.

6. A topical ophthalmic composition comprising an intraocular pressure lowering effective amount of travoprost, a prostaglandin synthesis inhibiting effective amount of nepafenac, and an ophthalmically acceptable vehicle therefore.

* * * * *